United States Patent
Voss et al.

(10) Patent No.: US 9,376,482 B2
(45) Date of Patent: Jun. 28, 2016

(54) METHOD FOR IMPROVING THE SPECIFIC EFFECTOR FUNCTION OF SINGLE-CHAIN ANTIGEN-RECOGNIZING GENETIC CONSTRUCTS (SCARC) THROUGH MURINIZATION THEREOF

(75) Inventors: Ralf-Holger Voss, Ingelheim (DE); Matthias Theobald, Mainz-Kastel (DE); Ratna Sari Intan Pöndl, Mainz (DE); Renate Engel, Mainz (DE); Simone Thomas, Mainz (DE)

(73) Assignee: Johannes Gutenberg-Universität Mainz, Mainz (DE)

(*) Notice: Subject to any disclaimer, the term of this patent is extended or adjusted under 35 U.S.C. 154(b) by 1242 days.

(21) Appl. No.: 12/439,431

(22) PCT Filed: Aug. 31, 2007

(86) PCT No.: PCT/EP2007/007631
§ 371 (c)(1),
(2), (4) Date: Nov. 25, 2009

(87) PCT Pub. No.: WO2008/028601
PCT Pub. Date: Mar. 13, 2008

(65) Prior Publication Data
US 2010/0143315 A1    Jun. 10, 2010

(30) Foreign Application Priority Data
Sep. 4, 2006 (DE) .................. 10 2006 041 455

(51) Int. Cl.
*C12N 15/62*   (2006.01)
*C12N 15/63*   (2006.01)
*C12P 21/00*   (2006.01)
*C07K 14/725*  (2006.01)
*C07K 16/00*   (2006.01)

(52) U.S. Cl.
CPC ............. *C07K 14/7051* (2013.01); *C07K 16/00* (2013.01)

(58) Field of Classification Search
CPC .... C07K 14/7051; C07K 19/00; C12P 21/00; C12N 15/62; C12N 15/63
USPC ............ 435/372.2, 325, 455, 456, 69.1, 69.6, 435/69.7
See application file for complete search history.

(56) References Cited

U.S. PATENT DOCUMENTS

2009/0304657 A1* 12/2009 Morgan et al. ............. 424/93.71

FOREIGN PATENT DOCUMENTS

| WO | WO 2004/056845 | * | 7/2004 |
| WO | WO 2004/056845 | * | 8/2004 |

OTHER PUBLICATIONS

Schaft et al. (2003) J. Immunol., vol. 170, 2186-2194.*
Blank et al. (1993) Eur. J. Immunol., vol. 23, 3057-3065.*
Cohen et al. (2006) Cancer Res., vol. 66(17), 8878-8886.*
Cohen et al. (2005) J. Immunol., vol. 175, 5799-5808.*
Pecorari et al., "Folding, heterodimeric association and specific peptide recognition of a murine αβ T-cell receptor expressed in *Escherichia coli*", *Journal of Molecular Biology*, 1999, vol. 285, No. 4, pp. 1831-1843.
Thomas et al., "Playing the game together: Coexpression of a single chain T cell receptor and a T cell receptor constant-alpha domain triggers tumor reactivity", *Blood*, 2006, vol. 108, Abstract 3716.
Voss et at, "Designing TCR for cancer immunotherapy", *Methods in Molecular Medicine*, 2005, vol. 109, pp. 229-256.
Voss et al., "Tumor-specific murine T cell receptors displace endogenous TCRs in human T cells", *Cancer Cell International*, 2004, vol. 4, No. Suppl. 1, p. S33.

* cited by examiner

*Primary Examiner* — Anne Marie S Wehbe
(74) *Attorney, Agent, or Firm* — Saliwanchik, Lloyd & Eisenschenk

(57) ABSTRACT

The present invention relates to a method for producing a cell line expressing a stabilized functional single chain-antigen-recognizing genetic construct (scARC), comprising a genetic construct of the human scARC to be expressed, comprising the domains $huV_{1/2}$—Li-$huV_{2/1}$—$C_{4/3}$ and a genetic construct comprising the corresponding hetero-/(homo-)dimeric domain $C_{3/4}$, containing xenogenic, in its special case murine amino acid exchanges in the domains $C_{4/3}$ and $C_{3/4}$, wherein co-expression of the genetic constructs of the scARC-fragments occurs through the cell. Preferably, the scARCs are single chain-TCRs (scTCRs) or antibody-scFv-fragments, which further preferably recognize tumor associated peptide antigens (TAA). The present invention further relates to a gp100-protein-specific T-cell response mediated α/β T-cell receptor rationally mutated by means of the method of the present invention and its uses.

30 Claims, 4 Drawing Sheets

Figure 2A:
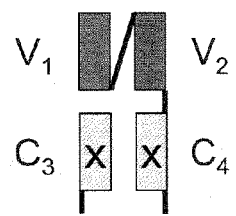

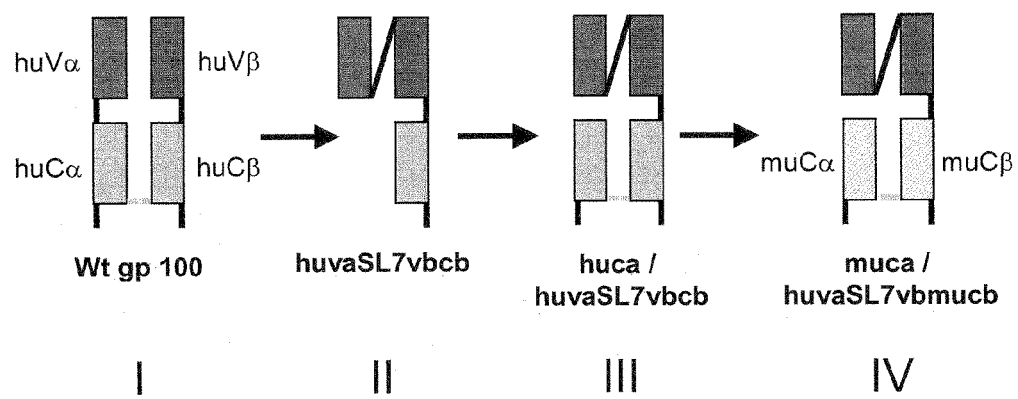
Fig1: Example for a human (hu) single chain-TCR, murinized (mu) in the constant domains, in co-expression with a constant murine Calpha-domain Figure 2: Models for scARCs modifed in $C_3/C_4$, provided with xenogenic (x) point mutations Surface expression of human gp100.280-288-specific TCR-constructs (FACS-analytics)

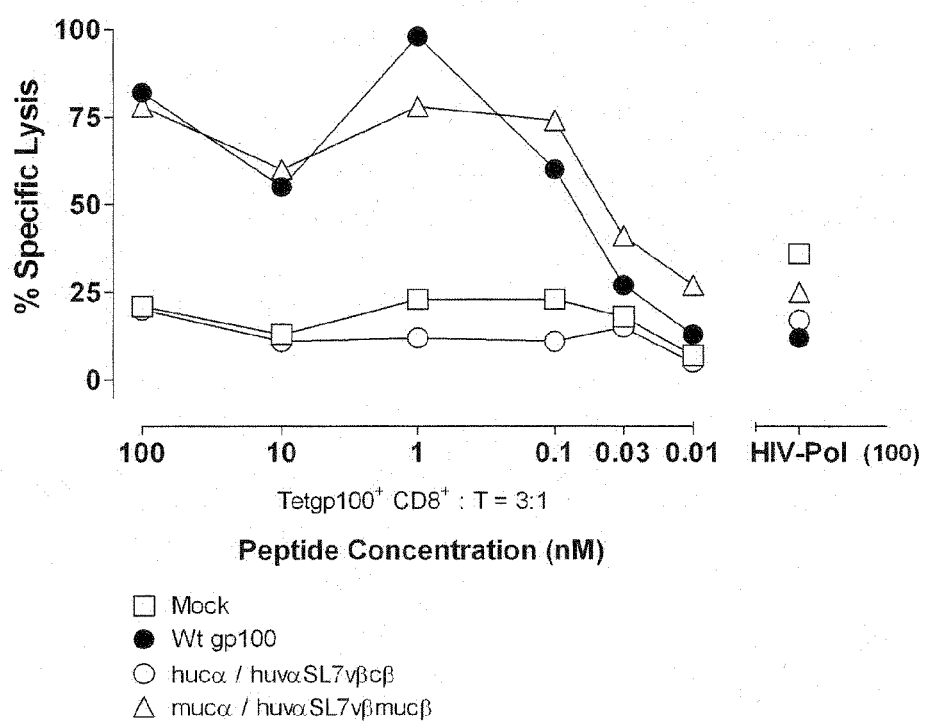
Fig 4: Cytolytic activity of human gp100.280-288-specific TCR-constructs (chromium release assay)

SEQUENCE LISTING

```
<160> NUMBER OF SEQ ID NOS: 4

<210> SEQ ID NO 1
<211> LENGTH: 1308
<212> TYPE: DNA
<213> ORGANISM: artificial
<220> FEATURE:
<223> OTHER INFORMATION: mutated scTCR construct
      (Valpha-Linker-Vbeta-Cbeta)

<400> SEQUENCE: 1
atggcatcca ttcgagctgt atttatattc ctgtggctgc agctggactt ggtgaatgga      60
gagaatgtgg agcagcatcc ttcaaccctg agtgtccagg agggagacag cgctgttatc     120
aagtgtactt attcagacag tgcctcaaac tacttccctt ggtataagca agaacttgga     180
aaaagacctc agcttattat agacattcgt tcaaatgtgg gcgaaaagaa agaccaacga     240
attgctgtta cattgaacaa gacagccaaa catttctccc tgcacatcac agagacccaa     300
cctgaagact cggctgtcta cttctgtgca gcaagtactt cgggtggtac tagctatgga     360
aagctgacat ttggacaagg gaccatcttg actgtccacg gcaccagcgg cagcagtggt     420
agcggcagcg gtggcagcgg tagtggcggt ggcggccaag tgacccagaa cccaagatac     480
ctcatcacag tgactggaaa gaagttaaca gtgacttgtt ctcagaatat gaaccatgag     540
tatatgtcct ggtatcgaca agacccaggg ctgggcttaa ggcagatcta ctattcaatg     600
```

```
aatgttgagg tgactgataa gggagatgtt cctgaagggt acaaagtctc tcgaaaagag    660
aagaggaatt tcccctgat  cctggagtcg cccagcccca accagacctc tctgtacttc    720
tgtgccagca gtttggggag ctcctacgag cagtacttcg gccgggcac  caggctcacg    780 gttttagagg atctgagaaa tgtgactcca cccaaggtct ccttgtttga gccatcaaaa    840
gcagagattg caaacaaaca aaaggctacc ctcgtgtgct tggccagggg cttcttccct    900
gaccacgtgg agctgagctg gtgggtgaat ggcaaggagg tccacagtgg ggtcagcacg    960
gaccctcagg cctacaagga gagcaattat agctactgcc tgagcagccg cctgagggtc   1020
tctgctacct tctggcacaa tcctcgaaac cacttccgct gccaagtgca gttccacggg   1080
ctttcagagg aggacaagtg gccagagggc tcacccaaac ctgtcacaca gaacatcagt   1140
gcagaggcct ggggccgagc agactgtgga atcacttcag catcctatca tcaggggggtt  1200 ctgtctgcaa ccatcctcta tgagatccta ctggggaagg ccaccctata tgctgtgctg   1260
gtcagtggcc tggtgctgat ggctatggtc aagaaaaaaa attcctga               1308
```

```
<210> SEQ ID NO 2
<211> LENGTH: 471
<212> TYPE: DNA
<213> ORGANISM: artificial
<220> FEATURE:
<223> OTHER INFORMATION: mutated TCRalpha construct
      (Signal peptide-Calpha)

<400> SEQUENCE: 2
```

```
atggaaaggc tgctgtgctc tctgctgggg cttctgtgca cacaggtttg ctgggtgaaa     60
ggacagaacc cagaacctgc tgtgtaccag ttaaaagatc ctcggtctca ggacagcacc    120
ctctgcctgt tcaccgactt tgactcccaa atcaatgtgc cgaaaaccat ggaatctgga    180
acgttcatca ctgacaaaac tgtgctggac atgaaagcta tggattccaa gagcaatggg    240
gccattgcct ggagcaacca gacaagcttc acctgccaag atatcttcaa agagaccaac    300
gccacctacc ccagttcaga cgttccctgt gatgccacgt tgactgagaa agctttgaa     360 acagatatga acctaaactt tcaaaacctg tcagttatgg actccgaat  cctcctgctg    420 aaagtagccg gatttaacct gctcatgacg ctgaggctgt ggtccagttg a             471
```

```
<210> SEQ ID NO 3
<211> LENGTH: 435
<212> TYPE: PRT
<213> ORGANISM: artificial
<220> FEATURE:
<223> OTHER INFORMATION: mutated scTCR (Valpha-Linker-Vbeta-Cbeta)
      peptide

<400> SEQUENCE: 3
```

```
Met Ala Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
```

```
                        85                  90                  95
Thr Glu Thr Gln Pro Glu Asp Ser Ala Val Tyr Phe Cys Ala Ala Ser
            100                 105                 110

Thr Ser Gly Gly Thr Ser Tyr Gly Lys Leu Thr Phe Gly Gln Gly Thr
        115                 120                 125

Ile Leu Thr Val His Gly Thr Ser Gly Ser Ser Gly Ser Gly Ser Gly
    130                 135                 140

Gly Ser Gly Ser Gly Gly Gly Gln Val Thr Gln Asn Pro Arg Tyr
145                 150                 155                 160

Leu Ile Thr Val Thr Gly Lys Lys Leu Thr Val Thr Cys Ser Gln Asn
                165                 170                 175

Met Asn His Glu Tyr Met Ser Trp Tyr Arg Gln Asp Pro Gly Leu Gly
            180                 185                 190

Leu Arg Gln Ile Tyr Tyr Ser Met Asn Val Glu Val Thr Asp Lys Gly
        195                 200                 205

Asp Val Pro Glu Gly Tyr Lys Val Ser Arg Lys Glu Lys Arg Asn Phe
    210                 215                 220

Pro Leu Ile Leu Glu Ser Pro Ser Pro Asn Gln Thr Ser Leu Tyr Phe
225                 230                 235                 240

Cys Ala Ser Ser Leu Gly Ser Ser Tyr Glu Gln Tyr Phe Gly Pro Gly
                245                 250                 255

Thr Arg Leu Thr Val Leu Glu Asp Leu Arg Asn Val Thr Pro Pro Lys
            260                 265                 270

Val Ser Leu Phe Glu Pro Ser Lys Ala Glu Ile Ala Asn Lys Gln Lys
        275                 280                 285

Ala Thr Leu Val Cys Leu Ala Arg Gly Phe Phe Pro Asp His Val Glu
    290                 295                 300

Leu Ser Trp Trp Val Asn Gly Lys Glu Val His Ser Gly Val Ser Thr
305                 310                 315                 320

Asp Pro Gln Ala Tyr Lys Glu Ser Asn Tyr Ser Tyr Cys Leu Ser Ser
                325                 330                 335

Arg Leu Arg Val Ser Ala Thr Phe Trp His Asn Pro Arg Asn His Phe
            340                 345                 350

Arg Cys Gln Val Gln Phe His Gly Leu Ser Glu Glu Asp Lys Trp Pro
        355                 360                 365

Glu Gly Ser Pro Lys Pro Val Thr Gln Asn Ile Ser Ala Glu Ala Trp
    370                 375                 380

Gly Arg Ala Asp Cys Gly Ile Thr Ser Ala Ser Tyr His Gln Gly Val
385                 390                 395                 400

Leu Ser Ala Thr Ile Leu Tyr Glu Ile Leu Leu Gly Lys Ala Thr Leu
                405                 410                 415

Tyr Ala Val Leu Val Ser Gly Leu Val Leu Met Ala Met Val Lys Lys
            420                 425                 430

Lys Asn Ser
        435

<210> SEQ ID NO 4
<211> LENGTH: 156
<212> TYPE: PRT
<213> ORGANISM: artificial
<220> FEATURE:
<223> OTHER INFORMATION: mutated TCRalpha (Signal peptide-Calpha)
      peptide

<400> SEQUENCE: 4
```

-continued

```
Met Glu Arg Leu Leu Cys Ser Leu Leu Gly Leu Leu Cys Thr Gln Val
1               5                   10                  15

Cys Trp Val Lys Gly Gln Asn Pro Glu Pro Ala Val Tyr Gln Leu Lys
            20                  25                  30

Asp Pro Arg Ser Gln Asp Ser Thr Leu Cys Leu Phe Thr Asp Phe Asp
            35                  40                  45

Ser Gln Ile Asn Val Pro Lys Thr Met Glu Ser Gly Thr Phe Ile Thr
    50                  55                  60

Asp Lys Thr Val Leu Asp Met Lys Ala Met Asp Ser Lys Ser Asn Gly
65                  70                  75                  80

Ala Ile Ala Trp Ser Asn Gln Thr Ser Phe Thr Cys Gln Asp Ile Phe
                85                  90                  95

Lys Glu Thr Asn Ala Thr Tyr Pro Ser Ser Asp Val Pro Cys Asp Ala
                100                 105                 110

Thr Leu Thr Glu Lys Ser Phe Glu Thr Asp Met Asn Leu Asn Phe Gln
            115                 120                 125

Asn Leu Ser Val Met Gly Leu Arg Ile Leu Leu Leu Lys Val Ala Gly
        130                 135                 140

Phe Asn Leu Leu Met Thr Leu Arg Leu Trp Ser Ser
145                 150                 155
```

METHOD FOR IMPROVING THE SPECIFIC EFFECTOR FUNCTION OF SINGLE-CHAIN ANTIGEN-RECOGNIZING GENETIC CONSTRUCTS (SCARC) THROUGH MURINIZATION THEREOF

CROSS-REFERENCE TO A RELATED APPLICATION

This application is a National Stage Application of International Application Number PCT/EP2007/007631, filed Aug. 31, 2007; which claims priority to German Application No. 10 2006 041 455.1, filed Sep. 4, 2006; all of which are incorporated herein by reference in their entirety.

DESCRIPTION

The present invention relates to a method for producing a cell line expressing a stabilized functional single chain-antigen-recognizing genetic construct (scARC), comprising a genetic construct of the human scARC to be expressed comprising the domains $huV_{1/2}$—Li-$huV_{2/1}$—$C_{4/3}$, and a genetic construct comprising the corresponding hetero-/(homo-)dimeric domain $C_{3/4}$, containing xenogenic, in its special case murine amino acid exchanges in the domains $C_{4/3}$ and $C_{3/4}$, wherein the genetic constructs of the scARC-fragments are co-expressed by the cell (FIG. 1). Preferably, the scARCs are single chain-TCRs (scTCRs) or antibody-scFv-fragments, which further preferably recognize tumor associated peptide antigens (TAAs). The present invention further relates to a gp100-protein-specific T-cell response mediated α/β T-cell receptor that is rationally mutated by means of the method of the present invention, and uses thereof.

Currently, the adoptive T-cell-transfer is a matter of intensive research in the immunotherapy of malign diseases. Hereby, one the one hand, autologous tumor-infiltrating lymphocytes of a tumor patient are isolated which are suspected to show a tumor-specific cytolytic reactivity, massively expanded ex vivo, and re-infused into the patient. Due to the fact that these TILs usually are of a lower reactivity, due to the low affinities of the respective T-cell-receptor (TCR), or anergetizing mechanisms, using other methods highly affine T-cell-receptors are isolated and developed and these are introduced into autologous human peripheral blood monocytes (PBMC) using, for example, retroviral gene transfer.

The native TCR is a membrane-based heterodimer of an alpha- and beta-chain, which are connected through a disulfide-bridge. The TCR recognizes a tumor-associated antigen (TAA) embedded in the MHC-molecule, and initializes a signaling cascade, which in CD8+-T-cells triggers the cytolytic activity directed against the target-cell, and in CD8+ and CD4+ cells triggers an accessory cytokine-supporting effector function. The target cells, such as, for example, the tumor cell, are driven into the programmed cell death (apoptosis).

A major problem is represented by the possibility that these exogenously introduced TCRs can interact with the endogenous TCRs, and thus exhibit undesired self-reactivities (1).

In order to avoid this, in the past single chain-T-cell-receptors have been developed, in which the variable domains Valpha and Vbeta of both chains are covalently linked through a connecting amino acid-linker. At the variable Vbeta-domain, mostly the constant Cbeta-domain is bound, to which, in turn, a signaling molecule such as, for example, the CD3-zeta-chain is bound, in order to functionally initiate the TCR-construct. A disadvantage of these constructs is the considerable chimeric character, and, regarding this, it can not be sufficiently said to what extent the natural signaling of a T-cell is modified.

One solution for avoiding the undesired pairing of chains is the design of single chain-T-cell-receptors. This scTCR-concept serves to prevent the undesired pairing of endogenous to exogenous chains. Using genetic engineering such constructs can be freely designed, and ensure a covalent 1:1-stoichiometry of the heterodimeric, variable domains. The scTCR-concept was initially developed for antibodies (2), but could be transferred to the former due to the structural homologies between antibodies and T-cell-receptors (3, 4). Hereby, the variable domains are covalently connected by a short peptide, a "linker", whereby one of both constant domains is omitted. Using genetic engineering such constructs can be freely designed, and ensure a biochemically coupled 1:1-stoichiometry of the heterodimeric variable domains.

Alternatively, using genetic engineering, short peptide sequences are added as affinity-tags to the respective chains of the heterodimeric molecule that provide for a specific pairing of chains: for this, a 30 amino acids long, carboxy-terminal "tag", a so-called "leucine zipper", was added to T-cell-receptors as a dimerization motif (5). In the past, it could be found that the stability and functionality of the scTCRs could be considerably improved through coupling to the full-length ζ-chain of the CD3-complex (4). Also, double-chain-TCRs fused to the CD3ζ-chain are used. Furthermore, invariant domains of different-function (membrane) proteins are used in place of the constant TCR-domain: CH2/CH3 of antibodies (6), the trans-membrane of the co-receptor CD4 (7), the membrane-anchoring/signaling domain of the FcεRIγ-receptor (8). A large number of the constructs as tested lagged behind the efficiencies and specificities of their wild type constructs (9).

An alternative way is through influencing the preferential pairing of chains through the introduction of artificial disulfide bridges (10), but due to the steric complementarity as present still has the disadvantage of undesired hybrid-pairing of chains with the endogenous chains.

Among the TAAs that are presented on the surface of tumor cells in the context of MHC-class-I-molecules, the so-called "universal" TAAs are of particular interest. These TAAs are mainly derived from cellular proteins that are weakly expressed in normal cells, and overexpressed in tumor cells. Amongst others, the human gp100-protein belongs to these proteins, playing a role, for example, in melanomas, glioblastomas or colorectal cancer (11).

Oligopeptides of the gp100-protein can be presented in the context with MHC-class-I-molecules on the surface of the cell, and represent attractive target structures for CD8-positive T-cells. Hereby, the extent of the T-cell response is found in a defined kinetic window (12). The complex of peptide-MHC and TCR-CD3 multimerizes in order to effect an efficient signal transduction, wherein the exact stoichiometry and the extent of the oligomerization is still under controversy.

The main disadvantage of the scTCR-CD3ζ-constructs is their requirement for coupling to the actual signaling molecule, CD3ζ, of the T-cell. This could represent a risk for T-cell-activation, from which allo-reactivities (autoimmune reactions) could result. Furthermore, the chimeric character of the scTCR-CD3ζ-chains is increased to such an extent that immune reactions against the foreign protein, in particular against the area of fusion to the human CD3ζ-chain, are to be expected.

DE 199 10 419 A1 describes multivalent proteins that are specific for target cells and consist of 3 components (a-c), wherein (a) is at least one drug, (b) is one or more linker, and (c) is at least 2 binding structures. The binding structures can be, for example, recombinant antibodies or parts thereof, but also transmembrane domains. The multivalent proteins of DE 199 10 419 A1 can contain signal sequences.

DE 695 22 216 T2 describes target cell-binding chimeric peptides, in particular recombinant antibody molecules with immuno-dominant peptide sequences, wherein the immuno-dominant peptide sequences are internalized and processed by the target cell, and subsequently are presented, leading either to an induction or to an inhibition of an immune reaction.

These antibody molecules containing immuno-dominant peptides can be obtained through, amongst others, co-expression.

Novotny et al. 1991 (Novotny J, Ganju R K, Smiley S T, Hussey R E, Luther M A, Recny M A, Siliciano R F, Reinherz E L. A soluble, single-chain T-cell receptor fragment endowed with antigen-combining properties. Proc Natl Acad Sci USA. 1991 Oct. 1; 88(19):8646-50) describe single-chain T-cell receptors (scTCRs) that contain both variable domains of a TCR, $V_{alpha}$ and $V_{beta}$, that are connected by a peptide linker. Furthermore, the TCRs contain a pelB-sequence for periplasmatic bacterial expression. Despite this, the scTCRs were obtained as insoluble protein in form of inclusion bodies that were first dissolved and purified by means of HPLC, and subsequently refolded using glutathione.

Plaksin et al. 1997 (Plaksin D, Polakova K, McPhie P, Margulies D H. A three-domain T cell receptor is biologically active and specifically stains cell surface MHC/peptide complexes. J Immunol. 1997 Mar. 1; 158(5):2218-27.) also describe an scTCR, which, nevertheless, is composed of 3 domains of a TCR being specific for an HIV-gp120-derived peptide complexed with mouse-MHC I. Thereby, the variable domain Valpha is linked with 2 domains of the beta-chain (Vbeta and Cbeta) through a peptide-linker. These 3-domain scTCRs were also expressed in *E. coli* in insoluble form, subsequently dissolved from the inclusion bodies, and refolded by means of glutathione using a laborious and time-consuming process. The scTCR showed a moderate affinity (in the μM-range) against the specific peptide/MHC I-complex.

Furthermore, techniques are known in the state of the art, whereby murine antibodies are humanized, i.e. components of initially murine antibodies are replaced with human parts. Through humanizing of monoclonal antibodies of the mouse, the known disadvantages of "classical" murine antibodies can largely be eliminated, since the body does no longer more or less strongly recognize these as "foreign". A similar situation can be found with TCRs (13, 14). Thus, there is a constant practice in the state of the art to replace murine with human sequences.

An alternative method was presented in DE 102 59 713.8 ("Method for stabilizing single-chain T-cell receptors"), wherein the missing Calpha domain is co-expressed as truncated TCRalpha-chain together with the single-chain-TCR. The functionality is given without a fusion to a signaling molecule. Nevertheless, this method is limited to murine single-chain-TCRs and could not be extended to a human scTCR plus co-expressed human Calpha. Thereby, particularly preferred according to DE 102 59 713.8 is an scTCR-chain or scFv-fragment that is humanized, leading, amongst others, to an improved tolerability of the TCR or fragment.

In view of the above, it is an object of the present invention to provide a method that allows for the production of a single chain-antigen-recognizing recombinant genetic construct (scARC) with an improved stabilization also in human scARCs, so that, for example during the production of recombinant scTCRs, no mixed pairs can be formed with the endogenous chains of the T-cells. In addition to the stabilization of the cell-surface expression of the scTCRs, a measurable—and in particular a specific—effector function of the human T-cell should be achieved. The method of the stabilization through the suitable co-expression should furthermore be applicable to other single-chain-antigen-recognizing recombinant genetic constructs, such as, for example, scFv-fragments (2).

According to the invention, this object is solved by a method for producing a stabilized functional single chain-antigen-recognizing genetic construct (scARC) expressing cell line, comprising a) providing a suitable host cell, b) providing a genetic construct of the human scARC to be expressed, comprising the domains $V_{1/2}$—Li—$V_{2/1}$—$C_{4/3}$ $V_1$—Li—$V_2$—$C_4$ or $V_2$—Li—$V_1$—$C_3$, and providing a genetic construct comprising the corresponding hetero-/(homo-)dimeric domain $C_{3/4}$ $C_3$ or $C_4$, containing murine amino acid exchanges in the domains $C_{4/3}$ and $C_{3/4}$, c) introducing directly or indirectly the genetic constructs through viral or non-viral gene transfer into a recombinant cell, and, d) co-expressing the genetic constructs of the scARC-fragments by the cell.

As one reason for the failure of the method as described in DE 102 59 713.8, it is assumed that the competitive pressure between the endogenous TCRalpha-chain and the artificial Cal-pha-construct for the incorporation into the essential CD3-complex that latter is largely displaced. Human native double chain-TCRs (dcTCRs) form hybrid pairs with endogenous TCRs a lot easier, and this reduces the surface-expression of the TAA-specific heterodimer, particularly in case of a truncated Calpha-domain (14, 15). The murinization of the constant domain in the truncated Calpha-domain and the Cbeta-domain in the single chain-TCR-construct causes a preferential interaction of the foreign species-chains, and thus their preferred incorporation into the CD3-complex. This finally supports its export to the cellular membrane.

Therefore, according to the invention, the human scTCR plus Calpha is functionally obtained through the components of the murine TCR. A "murinization" of the human scTCR plus Cal-pha means that corresponding amino acid exchanges, as present in the mouse-constant domain, are transferred into the human constant domains of the scTCR plus Calpha. In the maximal case, the constant domains of the scTCR plus Calpha are replaced by murine domains. In general, as many murine exchanges are introduced into the constant domain as are required for the effective competitive replacement of the endogenous TCR-alpha chain and the Calpha-construct. The person of skill is readily able to determine and to define the number of exchanges that is effective in the respective case. These exchanges are found in both recombinant constructs, since they shall promote the specific pairing. It is possible to also introduce xenogenic, that is, in comparison with the human sequence foreign-species, point mutations that differ from the mouse-sequences, but that provide for a comparable positive effect on the preferential interaction of the TCR and their incorporation into the CD3-complex.

It is also possible that scARCs of human origin are employed, which, nevertheless, have beestrongly in the variable antigen-recognizing domains thereof, for example through affinity maturation, such as phage display (10) or other interventions, that these are to be designated as merely of original-human origin. It is also possible that scARCs from other species (in general mammals) are used that are strongly modified through sequence-modifications and are suitable for the clinical use. Thus, the term "xenogenic" amino acid exchanges in the constant domains generally designates species specific differences between variable and constant domains.

Since the constant domain is the one domain being responsible for the membrane anchoring and the coupling to CD3, these domains were exemplary introduced into a human scTCR with the gp100.280-288-specificity that is highly-affine as native TCR, and the murine Calpha domain was co-expressed (FIG. 1). Both murine domains are materially essential for membrane anchoring and CD3-complex-integration (16).

The approach according to the invention is therefore based on a stabilization of the expression of single chain-TCRs (scTCRs) through co-expression of the hetero-/(homo-)dimeric constant murinized domain as binding partner, and on a stabilization of the expression of scFv-fragments through co-expression of the hetero-/(homo-)dimeric murinized constant domain as binding partner.

Preferred is method that further comprises the presentation of the stabilized heterodimeric scARC by the cell.

A further preferred aspect of the present invention thus also relates to a method for producing a stabilized single chain-TCR (scTCR). Said method comprises the steps as mentioned above, and furthermore the purification of the scARC from the cell, and, optionally, the reconstitution of the translated scARC-fragments in a T-cell.

As preferred by the present invention, a murinized Cα-domain was designed that can be co-transferred with an scTCR, and thus co-expressed. With this, a stabilization of the cell-surface expression of the scTCR and a measurable effector function of the human T-cell should be achieved. In addition, hereby an undesired pairing with endogenous chains can be avoided. After the introduction of the combinations of chains into human T-cells, these had to be tested with respect to their structural avidity, i.e. their structural integrity, as well as in view of their functional avidity, i.e. the maintenance of the peptide-dependent effector function (17). The human gp100(280-288)-specific T-cell-receptors served as a model system. The additionally present constant murinized domain that was missing in the respective scTCRs, served for a stabilization of the single chain-T-cell-receptor. With the increase of the stability, an improvement of the expression and the functionality in the context of the T-cell-effector function is affiliated (regarding this, see Figures).

Through the stabilizing effect of the additional constant domain in combination with an scTCR, it became possible to develop functional chimeric receptors without a mandatory fusion to the CD3ζ-chain.

The co-transduction with (e.g.) Cα completes the four extra-cytosolic domains Cα, Cβ, Vα, Vβ as present in the wild type-TCR, and exclusively modifies the linking of these four domains. Thus, no structural difference results in the cytosolic and trans-membrane regions as the essential, signal-inducing sites of effects, compared with the heterodimeric wild type-TCR, in sharp contrast to the TCR-CD3ζ-concept. An analogous concept exists for the case of the completion of constant domains in scFv-fragments. In addition, the fraction of the variable domains of the scARCs that serves for antigen recognition, is not sterically hindered by the co-expressed domains.

Particularly preferred is a method of the present invention, wherein the scARC is a single-chain-TCR (scTCR) or an antibody scFv-fragment.

Particularly preferred is a method of the present invention, wherein the cell is a mammalian, in particular human, T-cell. Further preferred, the scTCR is co-expressed in the orientation SP-Vα-Linker-Vβ-Cβ together with the constant domain SP-Cα or the scARC is co-expressed in the orientation SP-Vβ-Linker-Vα-Cα together with the constant domain SP-Cβ. These pairings then form optimally stabilized and correctly paired scTCR. Normally, the signal peptide (SP) is cleaved off in the endoplasmatic reticulum (ER), nevertheless, can be furthermore existent in artificial fusions to the membrane protein.

In addition to the MHC-restringed scTCR-concept, the above-mentioned scFv-concept allows for the MHC-independent recognition of antigens: here, the antigen-specific variable domains of the heavy and light chain of an antibodies are linked by means of a linker having a length of at least 14 amino acids, and, usually, by a "hinge"-region that serves as a spacer to the cellular membrane, fused to a membrane-localized signaling molecule of the CD3ζ-chain or the γ-chain of the immunoglobulin-receptor FcR. The "hinge"-region of CD8, the "hinge"-region of IgG1, or the immunoglobulin-like domains $C_{H2}C_{H3}$ of antibodies (7), respectively, function as spacers. The scFv-concept implies that any of the above-mentioned "hinge"-regions can be chimerized with any of the above-mentioned signaling components, and these can be fused to an arbitrary antigen(Ag)-specific single chain-Fv-fragment. The concept for a stabilization and functional improvement of single-chain-TCRs through the omission of the signaling component (CD3 ζ) by means of the complementary murinized constant domain as described here can be projected on the scFv-concept: scFv-fragments are, for example, fused to the murine constant Cβ of an arbitrary TCR, and are co-transferred in analogy with a murine Cα-domain. It is also intended to use the $C_{H2}C_{H3}$-domains of an antibody that are chimerized on one side with the scFv and on the other side with the membrane-localized domain of a TCR. Thus, a chimera of SP-$C_{H2}C_{H3}$-TM(TCR)-Cyt(TCR) is produced (abbreviation see explanation below) that heterodimerizes as the complementary domain with the chimeric scFv (18). In analogy to the natural situation with an antibody, the $C_{H2}C_{H3}$-domains homodimerize through the formation of a bivalent antigen-specific molecule. Both $C_{H2}C_{H3}$-domains as well as Cα/Cβ-domains form stabilizing disulfide bridges with each other. It is also possible to heterodimerize the $C_L$-domain of the light chain localized in the Fab-fragments of antibodies with the $C_{H1}$-domain of the heavy chain.

All these constant domains as described have in common their immunoglobulin-like folding and their tendency to stabilize with a complementary domain through homo- or heterodimerization, respectively. As examples, the following TCR-derived as well as antibody-derived chimeras are conceivable:

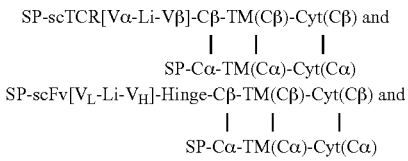

SP=signal peptide
$V_L$=$F_V$-Fragment of the light chain of an antibody
$V_H$=$F_V$-Fragment of the heavy chain of an antibody
Hinge=Hinge region from antibodies
TM(Cβ)=Trans-membrane of the murinized constant domain of a β-chain TCR
Cyt(Cβ)=Cytoplasmic part of the murinized constant domain of a β-chain TCR The description in the square brackets specifies the single chain(sc)-construct indicated before. Vertical lines indicate interactions between neighboring domains.

The integration of a "hinge"-region taken from antibodies is not regarded as essential. The concept as described in this paragraph does not take into account the importance and need of the α-CPM-domain of the α-chain of a TCR in case of the use of $C_{H2}C_{H3}$ or $C_{H1}$ or $C_L$, respectively. Conceivable would be the integration of $C_{H2}C_{H3}$ or $C_{H1}$ or $C_L$, respectively, in place of the Cβ or Cα, respectively, as used in the above-drafted constructs. The orientation of the variable domains in the single chains (e.g. Vα—Li—Vβ versus Vβ—Li—Vα) is arbitrary, and not necessarily dictates the use of the constant domain being directly adjacent thereto (e.g. Vα, versus Vβ).

The concept called "T-body" comprises all chimeric double chain- and single chain-receptors, which, in addition to the membrane anchor as essential component, include variable domains of antigen-specific antibodies (anti-"body") (2) and are, for example, introduced into a thymocyte ("T"-cell) using viral and/or non-viral gene transfer.

Due to the possibility to work without the signaling CD3ζ-domain at the C-terminus of the scTCR- or scFv-chimeras, respectively, in the new method as introduced here, functionally different signaling molecules, such as, for example, the tyrosine kinases belonging to the syk-family, could be fused (19). Hereby, in addition to the maintenance of the conformational stability, an optimization of the signal transduction can be achieved.

A further aspect of the present invention relates to a method according to the invention, wherein the linker (Li) is selected from Li(Gly$_4$Ser)$_3$, Li218 (20), and LiSL7 (21). Nevertheless, also other suitable linkers can be used, since the method according to the invention is not limited to the linkers as mentioned here.

The method according to the invention can be used for all single chain-antigen-recognizing constructs. All antigens as recognized by these constructs can be used as antigens, such as, for example, disease-specific surface-antigens, such as, for example, TAAs or infection-specific surface-antigens, such as, for example, HIV-specific surface-antigens or CMV-specific surface-antigens. Of course, also other antigens can be used that are known to the person of skill.

The introduction into the T-target cells can take place in any known manner allowing for a subsequent expression of the stabilized scTCR by the T-cell. Strategies are, for example, through the induction of phagocytosis by the cells or a method, wherein the introduction takes place by lipid-mediated transfer, such as, for example through micelles or liposome-transfer. An overview about the use of liposomes can, amongst others, be found in the article Banerjee R. Liposomes: applications in medicine. J Biomater Appl 2001 July; 16(1):3-21. The transfer using micelles is known to the person of skill from numerous publications.

Thus, as finally conceived thereby an expression of the e.g. scTCR occurs outside of the expressing T-cell, and a subsequent introduction into the same of the scTCR and the heterologous constant domain as simultaneously present. In case of the in vitro translation, the translation can occur in cell free systems that are commercially available. The "translation", nevertheless, also includes a purely synthetic production of the peptide chains, which is explained in more detail in the context of the peptides below. In case of the in vivo translation this can take place in a suitable host cell, which was first transformed with an expression construct of the chain, and subsequently produces the same. Suitable vectors and methods for the expression are sufficiently known to the person of skill in the state of the art. Following expression, it can be required to either purify the expression products from the cells or to extract the products from the medium, into which they were optionally secreted by the host cell. Suitable host cells are also known and can be yeast, CHO-cells, insect cells, bacteria or others.

According to a further aspect of the present invention, both scARC-fragments can be localized on one genetic construct. Thereby, the scARC and the heterologous constant domain are expressed in the correct stoichiometry of 1:1.

Preferably, according to the invention an scARC provided with additional (functional) domains, or an scARC provided with alternative domains, e.g. an scARC provided with a different transmembrane domain as membrane anchor, is used as an scARC.

Preferably, according to the invention an alpha/beta scTCR, gamma/delta scTCR, a scTCR provided with additional (functional) domains, or a scTCR provided with alternative domains, e.g. with a different transmembrane domain as membrane anchor, is used as an scTCR. Thereby, the alpha- and beta-chains of a gp100(280-288)-specific scTCR can be used as alpha-chain and beta-chain. Based on this scTCR, the principle according to the invention could be successfully applied for the first time.

Preferred is furthermore a method according to the invention, wherein a retroviral vector, in particular pBullet, is used as transfection system. In the vectors also IRES-elements can be used (22).

A further aspect of the present invention relates to a stabilized scARC that is produced according to a method according to the present invention. Further particularly preferred is a stabilized scARC according to the invention that is a TAA-specific scTCR or a TAA-specific scFv-ARC, in particular a mutated gp100(280-288)-specific TCR. This stabilized scTCR according to the present invention can also be present in the form of a fusion protein, comprising the modified polypeptides or parts thereof according to the invention. The fusion protein can be characterized in that it comprises the ζ-region of CD3 or CD8 or CD16 or parts thereof, in particular the ζ-region of human CD3 or CD8 or CD16 or parts thereof. In particular, the fusion protein according to the invention can comprise the ζ-chain of the CD3-complex or ITAM-motifs of the ζ-chain or parts thereof, in particular the ζ-chain of human CD3 or parts thereof. The fusion protein can furthermore be characterized in that it comprises CD8α or the Lck-binding motif of CD8α or parts thereof, in particular of human CD8α.

A further aspect of the invention relates to an isolated nucleic acid comprising a sequence encoding for a murinized constant domain SP-Cα or constant murinized domain SP-Cβ1 or murinized SP-Cβ2 of a stabilized scTCR. This nucleic acid according to the invention can be a DNA, RNA, PNA (peptide nucleic acid) or p-NA (pyranosyl nucleic acid), preferably a DNA, in particular a double-stranded DNA with a length of at least 8 nucleotides, preferably with at least 18 nucleotides, in particular with at least 24 nucleotides. The nucleic acid can be characterized in that the sequence of the nucleic acid has at least one intron and/or a polyA-sequence. It can also be present in form of its antisense-sequence.

A further aspect of the invention further relates to a DNA- or RNA-vector molecule, comprising at least one or several nucleic acid(s) according to the invention, that can be expressed in cells. For the expression of the respective gene, in general a double-stranded DNA is preferred, wherein the DNA-region encoding for the polypeptide is particularly preferred. This region starts with the first start codon (ATG) localized in a Kozak consensus sequence (Kozak, 1987, Nucleic. Acids Res. 15:8125-48) until the next stop codon (TAG, TGA or TAA, respectively) that is present in the same reading frame to the ATG. An additional use of the nucleic acid sequences according to the invention is the construction of anti-sense oligonucleotides (Zheng and Kemeny, 1995, Clin. Exp. Immunol. 100:380-2) and/or ribozymes (Amarzguioui, et al. 1998, Cell. Mol. Life. Sci. 54:1175-202; Vaish, et al., 1998, Nucleic Acids Res. 26:5237-42; Persidis, 1997, Nat. Biotechnol. 15:921-2). With anti-sense oligonucleotides, one can reduce the stability of the nucleic acid according to the invention and/or inhibit the translation of the nucleic acid according to the invention. Thus, for example, the expression of the respective genes can be reduced in cells both in vivo and in vitro. Thus, oligonucleotides can be suitable as therapeutics. This strategy is, for example, also suitable for skin, epidermal and dermal cells, in particular when the antisense oligonucleotides are complexed with liposomes (Smyth et al., 1997, J. Invest. Dermatol. 108:523-6; White et al., 1999, J. Invest. Dermatol. 112:699-705). For the use as probe or as "antisense" oligonucleotide, a single-stranded DNA or RNA is preferred.

In addition to the natural nucleic acids isolated from cells, all nucleic acids according to the invention or parts thereof can also be produced synthetically. Furthermore, for performing the invention, a nucleic acid can be used that was produced synthetically. For this, the nucleic acid according to the invention, for example, can be chemically synthesized based on the protein sequences as described using the genetic code, e.g., according to the phosphotriester-method (see, e.g., Uhlmann, E. and Peyman, A. (1990) Chemical Reviews, 90, 543-584).

In general, oligonucleotides are rapidly degraded by endo- or exonucleases, in particular by the DNases and RNases as present in the cell. Thus, it is advantageous to modify the nucleic acid in order to stabilize it against degradation, so that a high concentration of the nucleic acid is maintained in the cell over a long period of time (WO 95/11910; Macadam et al., 1998, WO 98/37240; Reese et al., 1997, WO 97/29116). Typically, such a stabilization can be obtained by introducing one or several internucleotide-phosphorous groups or by introducing one or several non-phosphorous-internucleotides.

Suitable modified internucleotides are summarized in Uhlmann and Peymann (1990 Chem. Rev. 90, 544; WO 95/11910; Macadam et al., 1998, WO 98/37240; Reese et al., 1997, WO 97/29116). Modified internucleotide-phosphate residues and/or non-phosphorous bridges in a nucleic acid which can be used in one of the uses according to the invention contain, for example, methylphosphonate, phosphorothioate, phosphoramidate, phosphorodithioate, phosphate esters, whereas non-phosphorous-internucleotide-analogs contain, for example, siloxane bridges, carbonate bridges, carboxymethylesters, acetamidate bridges and/or thioether bridges. It is also intended that this modification improves the lifespan of a pharmaceutical composition that can be used in one of the uses according to the invention.

A further aspect of the present invention relates to a vector, preferably in the form of a plasmid, shuttle vector, phagemid, cosmid, expression vector, adenoviral vector, retroviral vector (Miller, et al. "Improved retroviral vectors for gene transfer and expression", BioTechniques Vol. 7, No. 9, p 980, 1989) and/or gene therapeutically effective vector containing a nucleic acid according to the invention.

Thus, the nucleic acid according to the invention can be contained in a vector, preferably in an expression vector or gene therapeutically effective vector. Preferably, the gene therapeutically effective vector contains T-cell-specific regulatory sequences, which are functionally linked to the nucleic acid according to the invention. The expression vectors can be prokaryotic or eukaryotic expression vectors. Examples for prokaryotic expression vectors are, for the expression in *E. coli*, e.g., the vectors pGEM or pUC-derivatives, and for eukaryotic expression vectors for the expression in *Saccharomyces cerevisiae*, e.g., the vectors p426Met25 or p426GAL1 (Mumberg et al. (1994) Nucl. Acids Res., 22, 5767-5768), for the expression in insect cells e.g. *Baculovirus*-vectors such as, for example, disclosed in EP-B1-0 127 839 or EP-B1-0 549 721, and for the expression in mammalian cells, e.g., the vectors Rc/CMV and Rc/RSV or SV40-vectors that are all generally available.

In general, the expression vectors also contain promoters that are suitable for the respective host cell, such as, for example, the trp-promoter for the expression in *E. coli* (see, e.g., EP-B1-0 154 133), the Met 25, GAL 1 or ADH2-promoter for the expression in yeasts (Russel et al. (1983), J. Biol. Chem. 258, 2674-2682; Mumberg, supra), the baculovirus-polyhedrine-promoter for the expression in insect cells (see, e.g., EP-B1-0 127 839). For the expression in mammalian cells, for example, promoters are suitable that allow for a constitutive, controllable, tissue-specific, cell cycle-specific or metabolism-specific expression in eukaryotic cells. Controllable elements according to the present invention are promoters, activator sequences, enhancer, silencer and/or repressor sequences. Examples for suitable controllable elements that allow for the constitutive expression in eukaryotes are promoters that are recognized by the RNA polymerase III, or viral promoters, CMV-enhancer, CMV-promoters, CMV-LTR-hybrids, SV40 promoters or LTR-promoters, e.g. of MMTV (mouse mammary tumor virus; Lee et al. (1981) Nature 214, 228-232), and additional viral promoter and activator sequences, derived, for example, from HBV, HCV, HSV, HPV, EBV, HTLV or HIV. One example for a controllable element that allows for a controllable expression in eukaryotes is the tetracycline operator in combination with a corresponding repressor (Gossen M. et al. (1994) Curr. Opin. Biotechnol. 5, 516-20).

Examples for controllable elements that allow for the T-cell specific expression in eukaryotes are promoter or activator sequences from promoters or enhancers of those genes that encode for proteins that are only expressed in these types of cells.

Examples for controllable elements that allow for the cell cycle-specific expression in eukaryotes are promoters of the following genes: cdc25, cyclin A, cyclin E, cdc2, E2F, B-myb or DHFR (Zwicker J. and Müller R. (1997) Trends Genet. 13, 3-6). Examples for controllable elements that allow for the metabolism-specific expression in eukaryotes are promoters that are regulated through hypoxia, glucose starvation, phosphate concentration, or heat shock.

The vector according to the invention can be used for a transfection of a host cell which, preferably, is a T-cell. Particularly preferred is a host cell that is characterized in that it expresses on its surface a stabilized scTCR or fusion protein or stabilized scFv-fragment according to the invention. An additional matter of the invention thus relates to a method for producing a polypeptide for a diagnosis and/or treatment of diseases that are related to oncoproteins, or for identifying of pharmacologically active substances in a suitable host cell, which is characterized in that a nucleic acid according to the invention is expressed in a suitable manner.

The polypeptide is, for example, produced through expression of the nucleic acid according to the invention in a suitable expression system, as already described above, in accordance with methods that are generally known to the person of skill. For example, the *E. coli* strains DH5, HB101 or BL21, the yeast strain *Saccharomyces cerevisiae*, insect cell lines, e.g. of *Spodoptera frugiperda*, or the animal cells COS, Vero, 293, HaCaT, and HeLa, which are all generally available, are suitable as host cells.

In order to allow for the introduction of nucleic acids according to the invention through transfection, transduction, transformation or infection, and thus the expression of the polypeptide in a eu- or prokaryotic cell, the nucleic acid can be present as a plasmid, as part of a viral or non-viral vector or particle. Hereby, particularly suitable as viral vectors or particles are: baculoviruses, vaccinia viruses, retroviruses, adenoviruses, adeno-associated viruses, and herpes viruses. Particularly suitable as non-viral carriers are: virosomes, liposomes, cationic lipids, or poly-lysine conjugated DNA.

Examples of gene-therapeutically effective vectors are viral vectors, for example adenoviral vectors or retroviral vectors (Lindemann et al., 1997, Mol. Med. 3: 466-76; Springer et al., 1998, Mol. Cell. 2: 549-58; (4)).

A preferred mechanism to express polypeptides according to the invention in vivo, is viral gene transfer, in particular with the aid of retroviral particles. These are preferably used in order to provide respective target cells, preferably T-lymphocytes, of the patient ex vivo by transduction with the genes or nucleotide sequences encoding for polypeptides according to the invention. Then, in the sense of an adoptive cell transfer, the target cells can be reinfunded into the patient again, in order to take over tumoricidal and/or immune-modulating effector functions with the de novo introduced specificity. Most recently, using this strategy very good gene therapeutic progresses in the treatment of SCID-X1-disease characterized by immuno-incompetence were achieved in newborns, whereby hematological precursor cells were provided retrovirally with an analogous intact transgene of a non-functional mutated variant of the γ-chain gene found in the children that is essential for the differentiation into the different effector cells of the adaptive immune system (23).

Furthermore, the possibility exists to perform the gene transfer in vivo, on the one hand bby preferential stereotactic injection of the infectious particle, on the other hand by direct application of virus-producing cells (Oldfield, et al. Hum. Gen. Ther., 1993, 4:39-69).

The viral vectors that are commonly used for a transfer of genes in accordance with today's state of the art are primarily retroviral, lentiviral, adenoviral, and adeno-associated viral vectors. These are circular nucleotide sequences derived from natural viruses, wherein at least the viral structural protein-encoding genes are replaced by the construct to be transferred.

Retroviral vector systems provide the prerequisites for a long-lasting expression of the transgene by a stable, but undirected, integration into the host genome. Vectors of the younger generation include no irrelevant and potentially immunogenic proteins, furthermore, no pre-existing immunity of the recipient against the vector is found. Retroviruses contain an RNA-genome that is packaged into a lipid coating that consists of parts of the host cell membrane and viral proteins. For the expression of viral genes, the RNA-genome is reversely transcribed, and integrated with the enzyme integrase into the target cell-DNA. This can then be transcribed and translated by the infected cell, whereby viral components are generated that assemble into retroviruses. Only in these cases RNA is introduced into the newly generated viruses. The genomes of the retroviruses include three essential genes: gag, encoding for viral structural proteins, so-called group-specific antigens, pol for enzymes, such as reverse transcriptase and integrase, and env for the envelope, which is responsible for the binding of the host specific receptor. The production of the replication-incompetent viruses after transfection takes place in so-called packaging cell lines that are additionally provided with the gag/pol-encoding genes, and express these "in trans", and therefore complement the formation of replication-incompetent (i.e. gag/pol-deleted) transgenic viral particles. An alternative is a co-transfection of the essential viral genes, whereby only the vector containing the transgene carries the packaging signal.

The separation of these genes on the one hand allows the arbitrary combination of the gal/pol-reading frame with env-reading frames obtained from different strains, whereby pseudotypes with modified host tropism are generated, on the other hand, thereby the formation of replication competent viruses within packaging cell lines can be drastically reduced. The envelope protein derived from the "gibbon ape leukemia virus" (GALV) that finds use in the "stitch" or "bullet"-vector system, respectively (4, 7), can transduce human cells and is established in the packaging cell line PG13 with amphotrophic host range. In addition, the safety is increased through a selective deletion of non-essential viral sequences in order to prevent a homologous recombination, and thus the production of replication competent particles.

Novel non-viral vectors consist of autonomous, self-integrating DNA-sequences, transposons, that are, e.g., introduced into the host cell through liposomal transfection, and which for the first time were successfully used for an expression of human transgenes in mammalian cells (24, 25).

Nevertheless, gene therapeutically effective vectors can also be obtained through complexing the nucleic acid according to the invention with liposomes, as thereby a very high transfection efficiency, in particular of skin cells, can be achieved (Alexander and Akhurst, 1995, Hum. Mol. Genet. 4: 2279-85). Auxiliary agents that increase the transfer of nucleic acids into the cell, can be, for example, proteins or peptides that are bound to DNA, or synthetic peptide-DNA-molecules that enable the transport of the nucleic acid into the nucleus of the cell (Schwartz et al. (1999) Gene Therapy 6, 282; Brandén et al. (1999) Nature Biotech. 17, 784). Auxiliary agents also comprise molecules that allow for the release of nucleic acids into the cytoplasm of the cell (Planck et al. (1994) J. Biol. Chem. 269, 12918; Kichler et al. (1997) Bioconj. Chem. 8, 213), or, for example, liposomes (Uhlmann and Peymann (1990) supra). A different particularly suitable form of gene therapeutic vectors can be obtained by coating the nucleic acid according to the invention onto gold particles, and shooting these using the so-called "gene gun" into tissue, preferably into the skin, or cells (Wang et al., 1999, J. Invest. Dermatol., 112:775-81).

It is further advantageous for the gene therapeutic use of the nucleic acid according to the invention, if the part of the nucleic acid encoding for the polypeptide contains one or several non-coding sequences, including intron sequences, preferably between promoter and the start codon of the polypeptide, and/or a polyA-sequence, in particular the naturally occurring polyA-sequence or an SV40 virus polyA-sequence, in particular at the 3'-end of the gene, as thereby a stabilization of the mRNA can be achieved (Jackson, R. J. (1993) Cell 74, 9-14, and Palmiter, R. D. et al. (1991) Proc. Natl. Acad. Sci. USA 88, 478-482).

A further aspect of the present invention relates to a host cell containing a DNA- or RNA-vector molecule according to the invention. This cell, in particular, can be a T-cell that is transformed with a vector according to the invention or another genetic construct according to the invention. Host cells can both be prokaryotic or eukaryotic cells, examples for prokaryotic host cells are *E. coli*, and *Saccharomyces cerevisiae* or insect cells for eukaryotic cells.

A further aspect thus relates to a recombinant T-cell that expresses at least one stabilized scTCR according to the present invention. A particularly preferred transformed host cell is a transgenic T-precursor cell or a stein cell, that is characterized in that it comprises a genetic construct according to the invention or an expression cassette according to the invention. Methods for the transformation or transduction of host cells and/or stem cells are well known to the person of skill and, for example, comprise electroporation or microinjection. A particularly preferred transformed host cell is a T-cell of the patient, which, following its isolation, is transfected with a genetic construct according to the invention. Host cells according to the invention can be particularly obtained in that one or more cells, preferably T-cells, in particular $CD8^+$-T-cells are taken from the patient, which in order to obtain host cells according to the invention are then transfected or transduced ex vivo with one or several genetic constructs according to the invention. The specific ex vivo generated T-cells can then be re-implanted into the patient. The method therefore is similar to the method as described in Darcy et al. ("Redirected perforine-dependent lysis of colon carcinoma by ex vivo genetically engineered CTL" J. Immunol., 2000, 164:3705-3712), using scFv anti-CEA receptor transduced CTL, Perforin and γ-IFN.

The modified (poly)peptide and its derivative according to the invention can, for example, be used further for the active and/or passive immunization of patients with diseases, in particular tumorous diseases, which are, for example, associated with gp100. A particularly preferred aspect of the present invention thus relates to said use, wherein a cancerous disease is treated, in particular a cancerous disease that is associated with a modified expression of gp100, in order to achieve the induction, production and increase of oncogene-specific, e.g. gp100-specific CTLs, and to specifically kill the tumorous and leukemia cells of the respective patient. Such diseases comprise, for example, solid tumorous diseases, lympho-hematopoietic neoplasias, malign hematological diseases, also in form of multiple myeloma (or plasmocytoma), histiocytic lymphoma, and CML-blast crisis. TAAs that are associated with these are, for example, p53, Her-2/neu, Ras, tyrosinase, MART, Gp100, MAGE, BAGE, MUC-1, TRP-1, TRP-2, CD45, CD19, and PRD1-BF1, against which the corresponding TCRs can be developed.

A particularly preferred aspect of the present invention thus also relates to a composition, in particular a pharmaceutical composition, comprising a recombinant T-cell according to the present invention. Furthermore preferred is the use of a stabilized scTCR according to the present invention, a mutated TCR according to the present invention, and/or a recombinant T-cell according to present invention, for producing therapeutics and/or prophylactics for a treatment of cancerous diseases. In a particularly preferred regimen of treatment, one or several cells, preferably T-cells, in particular $CD8^+$-T-cells, are taken from the patient, which then are transduced or transfected ex vivo with one or several genetic constructs according to the invention. The specific T-cells generated ex vivo can then subsequently be re-implanted into the patient. The composition according to the invention can furthermore contain suitable additives and excipients.

A matter of the present invention further is a medicament for the indication and therapy of diseases that are associated with oncoprotein-proteins, containing a nucleic acid or a polypeptide according to the invention and, optionally, containing suitable additives and excipients, as well as a method for producing such a medicament for the treatment of diseases that are associated with oncoprotein-proteins, wherein a nucleic acid according to the invention or a poly-peptide according to the invention is formulated with a pharmaceutically acceptable carrier. In particular vaccines, recombinant particles or injections or infusion solutions that contain as active ingredient (a) the stabilized scTCR-receptor polypeptide and/or its derivatives according to the invention and/or (b) a nucleic acid according to the invention, and/or (c) T-lymphocytes produced in vitro or ex vivo that contain a specific mutated scTCR directed against oncoproteins can be considered as therapeutics and/or prophylactics.

Particularly suitable is a medicament and/or recombinant particle for gene therapeutic use in humans containing the nucleic acid according to the invention in naked form or in form of a gene therapeutically effective vector as described above, or in complexed form with liposomes or gold particles, respectively. The pharmaceutical carrier is, for example, a physiological buffer solution, preferably with a pH of about 6.0-8.0, preferably of about 6.8-7.8, in particular of about 7.4 and/or an osmolarity of about 200-400 milliosmol/liter, preferably of about 290-310 milliosmol/liter. In addition, the pharmaceutical carrier can contain suitable stabilizers, such as, for example, nuclease inhibitors, preferably complex forming agents, such as EDTA and/or other excipients known to the person of skill.

It is conceivable to further improve the efficiency of the Cα/scTCR-concept through chimerization at signaling domains, such as CD3ζ or tyrosine kinases (e.g. Cα-ζ/scTCR-ζ). Several scTCR-constructs, independently of whether they are of human or murine origin, as well the nature of the linker and the chosen orientation of the variable domains are also taken into account in this approach.

In addition to their signaling function, CD3ζ-chains have the potential for a homodimerization, and thus facilitate the association of a chimeric Cαζ-chain with the chimeric scTCRζ (25). In addition to the exemplary approach as described here, a murinized human TCR of the orientation SP-$V_1$—Li—$V_2$—$C_4$ plus a co-expressed truncated $C_3$-domain (FIG. 2a), a further possibility exists to design inverse constructs of the orientation SP-$V_2$—Li—$V_1$—$C_3$ plus $C_4$, which in the exemplary case of a TCR contain a Cα-domain in place of the Cβ-domain, and are co-transfected in combination with an SP-Cβ-domain (FIG. 2b). It is furthermore conceivable to fuse arbitrary variable domains derived from antibodies or T-cell-receptors to arbitrary invariant domains in their function as a) spacer to the transmembrane, b) as dimerization domain, c) as membrane anchor, and d) as adapter protein to the signal coupling (FIG. 2c).

The concept as presented here is furthermore species-independent and can be transferred to human molecules. For a further generalization, xenogenic point mutations, in the special case whole domains of other species (e.g. rat, monkey, dog), are introduced into $C_3$ and $C_4$ providing a stabilizing effect on the avidity of the single chain-construct.

It is furthermore conceivable, to extend the scTCR stabilizing constant murinized domain-concept to single chain-antibodies (scFv) through co-expression of the complementary $CH_L$-or $C_L$-chain, respectively. The concept is thus general.

All TAA-specific TCRs that have been developed and will be developed that are to be used in the adoptive immunotherapy through gene transfer into human T-cells of tumor patients, can be developed with minimal effort in accordance with the model as described. Thus, the approach as presented here could find wide-spread use in the clinical application (23).

The term "stabilized scARC" refers to a stabilized single chain-antigen recognizing genetic construct (scARC), wherein in addition to the regular $V_{1/2}$—Li—$V_{2/1}$—$C_{4/3}$-scconstruct, a corresponding heterodimeric point-mutated or xenogenic, in the special case murinized, constant domain $C_{3/4}$ is co-expressed. Preferably the scARCs are stabilized single chain-TCRs (scTCRs), or stabilized antibody-scFv-fragments which further preferred recognize tumor associated peptide antigens (TAAs). The term "stabilized scTCR" refers to the combination of the respective scTCR, e.g., in the orientation SP-Vα—Li—Vβ-Cβ together with the constant domain SP-Cα, or the scTCR in the orientation SP-Vβ—Li—Vα-Cα together with the constant domain SP-Cβ. These pairings then form optimally stabilized and correctly paired scTCRs. Thereby, the stabilized scTCR can stem from the expression of one or two different genetic constructs.

The term "encoding nucleic acid" refers to a DNA-sequence that encodes for a isolatable bio-active polypeptide or a precursor according to the invention. The polypeptide can be encoded by a sequence in full length or any part of the encoding sequence, as long as the specific, for example, enzymatic activity is maintained.

It is known that small modifications in the sequence of the nucleic acids according to the invention can be present, for example due to the degeneration of the genetic code, or that non-translated sequences are added to the 5' and/or 3'-end of the nucleic acid, without that its activity is essentially modified. Therefore, this invention also encompasses so-called "functional variants" of the nucleic acids according to the invention.

"Stringent hybridization conditions" designate conditions, wherein a hybridization at 60° C. in 2,5×SSC-buffer takes place, followed by several washing steps at 37° C. in a lower buffer concentration, and remains stable.

The invention shall now be further explained with reference of the attached examples and figures, without being limited through these. In the Figures:

SEQ ID No. 1: shows the nucleic acid sequence of the single chain T-cell-receptor with the gp100.280-288-specificity of Hu Chim scTCR gp100 (scHuVaLiHuVβMuCβ), murinized in Cbeta, SEQ ID No. 2: shows the nucleic acid sequence of a murine truncated TCRalpha with signal peptide from TCRalpha of (Mu SpCa), SEQ ID No. 3: shows the protein sequence of Hu Chim scTCR gp100 (scHuVαLiHuVβMuCβ), and SEQ ID No. 4: shows the protein sequence of Mu SpCa, wherein hu=human, mu=murine, Li=linker, SP=signal peptide.

FIG. 1: Example of a human (hu), single chain-TCR murinized (mu) in the constant domains in co-expression with a constant murine Ca-domain In FIG. 1, I designates the structure of a native human (hu) TCR, consisting of two heterodimeric alpha- and beta-chains. Each chain is composed of 2 domains, wherein the variable domains (Vα/Vβ) are responsible for the antigen-recognition, and the constant domains (Cα/Cβ) are responsible for the membrane anchoring and coupling to the signaling CD3-complex. II designates a single chain-TCR-construct, wherein the variable domains are linked through a glycine/serine-rich linker 19 of amino acids in length. The Calpha-domain is missing; the membrane anchoring exclusively takes place through Cbeta. III designates a single chain-TCR-construct, wherein the human Calpha-domain is co-expressed independently. IV designates a chimeric single chain-TCR-construct, wherein the human Cbeta-domain was replaced by a murine Cbeta-domain. For reasons of complementarity, this is co-expressed also with a murine Calpha-domain.

FIG. 2: Models for modified scARCs that are provided with xenogenic (x) point mutations in C3/C4

Figure 2B:
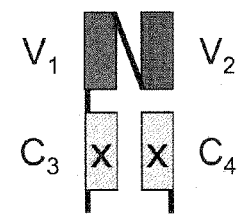
Figure 2C:
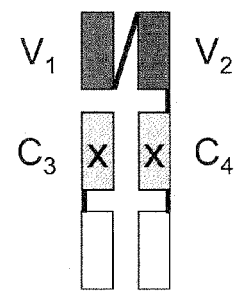

FIG. 2a/b illustrates the conceivable combinations of human variable domains ($V_1$ and $V_2$) and constant domains ($C_1$ and $C_2$) that are completely or in partially provided with xenogenic (X) amino acid exchanges. FIG. 2c illustrates the possible chimerization with functionally different, e.g. signaling, domains.

Figure 3:
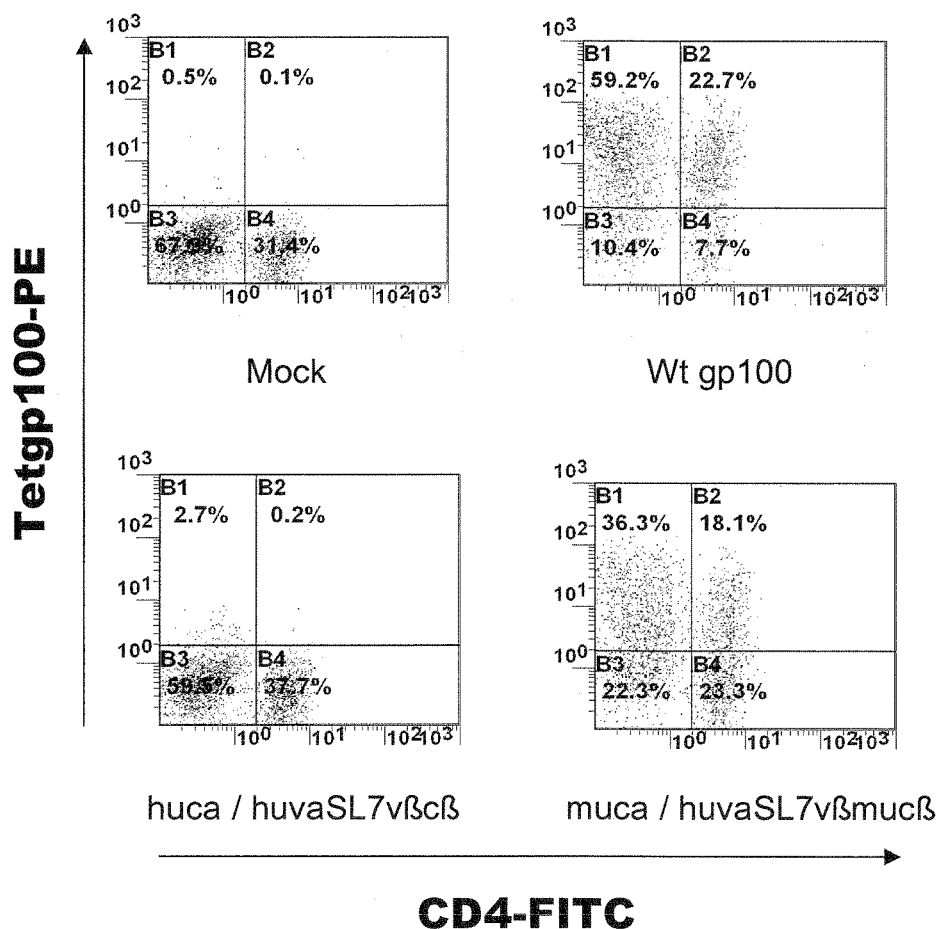

FIG. 3: Surface expression of human gp100.280-288 specific TCR-constructs (FACS-analytics)

FIG. 3 shows the analysis of the surface expression using FACS. Using a CD4-FITC-antibody, CD4+ and CD8+ T-cells are distinguished. All cells are CD3+, and thus T-cells. The tetramer consists of multimeric HLA-A2-molecules that are loaded with the gp100.280-288 —peptide. Constructs with intact structural avidity can bind to these. Mock designates the empty retroviral vectors, the other constructs can be taken from FIG. 1. In order to ensure a maximal expression, all transduction-preparations were selected for resistance against the antibiotics neomycin and puromycin. The co-expression of the human Calpha does not lead to a detection, only the murinization of both constant domains exhibits a detectable surface expression.

FIG. 4: Cytolytic activity of human gp100.280-288 specific TCR-constructs (chromium-release test)

FIG. 4 shows the analysis of the functional avidity using the radioactive chromium-release test. Constructs as designated in FIG. 1 have been tested for their ability to specifically recognize T2-target cells that are loaded with the relevant gp100-specific antigen in a dosage-dependent manner, compared with an irrelevant antigen. Depending on the efficiency of the construct, recombinant CD8+ T-cells lyse the target cells as recognized through perforin. The murinized construct IV of FIG. 1 is comparable in its lytic efficiency with the native TCR, despite lower expression (FIG. 2).

EXAMPLES

Regarding the production and respective molecular biological methods, reference can generally be made to the examples of DE 102 59 713.8.

In the context of the experiments for the present invention, the human scTCR plus Calpha was functionally obtained through components of the murine TCR. Since the constant domain is the domain that is responsible for membrane anchoring and coupling to CD3, this domain was introduced as a model into a human scTCR with the gp100.280-288-specificity which is highly affine as a native TCR, and the murine Calpha domain was co-expressed (FIG. 1). Both murine domains are essential for membrane anchoring and CD3-complex integration.

In contrast to the human scTCR plus human Calpha, which in FACS did not show any surface expression, the expression of the chimeric scTCR plus murine Calpha was clearly detectable (FIG. 2.: 36.3% of the CD8+ and 18.1% of the CD4+ T-cells). Likewise, a cytolytic activity that was clearly detectable above the background was measured in the chromium release test (FIG. 3). This was comparable with the wild type dcTCR, although the expression seems to be limited. No further improvement of the cytolytic activity was expected by the increase of the expression of highly-affine dcTCRs.

Based on the 100.280-288-specific TCR, this example shows the possibility to functionally initiate human single chain-TCRs through partial murinization in human T-cells, without increasing the chimerism of the molecule too much, that is, to modify it too much, and thus to increase the antigenicity and unspecific reactivity thereof.

It was shown in later experiments that in a construct according to the invention comprising an ecto-subdomain with a murine sequence and a transmembrane and cytosolic part with a human sequence, an activity was found that indeed was not as high as in a completely murinized constant domain according to the invention (see above), but, nevertheless, was still markedly pronounced, whereas in a construct comprising an ecto-subdomain with a human sequence and a transmembrane and cytosolic part with a murine sequence an activity was found that was nearly approaching zero. These experiments therefore clearly show the importance of the murinization of the ecto-subdomain.

Experimental Instructions:

Transduction of Human Peripheral Blood Lymphocytes (PBLS)

For a transduction of human peripheral T-lymphocytes, a functional derivative of the pStitch-system (Weijtens et al., 1999) was used. The genes that are required for a packaging are encoded by separate plasmids using a co-transfection of the packaging cell line 293T: pHit60 encodes for the gag-pol—structural and polymerase—genes from Moloney murine leukemia virus (MoMuLV), pColt-Galv for the env—envelope protein of the "gibbon ape leukemia virus", which is able to bind to the $Na^+$-/phosphate-synporter Pit of human cells, and thereby to transduce the latter. The chimeric viral particles thus have an amphotrophic pseudotype, and can transduce several mammalian cells, with the exception of mouse.

Transfection of the Packaging Cell Line 293T

The isolated bacterial clones of the T-cell-receptor-genes as cloned into the pStitch-derivative were purified using plasmid preparations, which ensure a removal of residual endotoxins (Qiagen, product 12362), and were adjusted at 0.5 µg/µl. The DNA was transiently introduced into the packaging cell line 293T (GiboBRL-Life Technologies, product 18306-019) using calcium phosphate-precipitation. Hereby, in the context of the stabilized T-cell-receptors αTCR and βTCR, up to 80 µg DNA were used:

20 µg αTCR-construct
20 µg βTCR-construct
20 µg pColt-Galv
20 µg pHit 60

In case of single chain-TCRs, 60 µg DNA were used. 293T was cultured in a modified DMEM-medium (DMEM/H):

DMEM, 4,5% glucose (BioWhittaker)
10% heat inactivated FCS
2 mM glutamine
1× penicillin/streptomycin
1× non-essential amino acids
25 mM HEPES On the day before the transfection, the 293T cells were seeded at $0.9*10^6$ cells in 5 ml DMEM/H per T25-flask and transfection preparation. 4 h before transfection, the medium was replaced with fresh DMEM-H (3 ml) that was warmed to room temperature (RT). The transfection took place in accordance with the commercial protocol (Invitrogen). 1 ml of the transfection preparation was pipetted into each flask through careful dripping. The DNA-$Ca_3(PO_4)_2$-precipitate should be spread out finely dispersed onto the adherent cells.

At the following morning, the medium was replaced with fresh DMEM/H that was warmed to RT. 6 h later, the co-cultivation with the activated PBLs was performed.

Transduction of Thee Activated Pbls—Activation of Peripheral Blood-Lymphocytes (PBLs)

3 days prior to the scheduled co-cultivation, Ficoll-treated PBLs were seeded at $2*10^6$ in huRPMI-P, each in 2 ml in a 24 well-plate (cell tissue-treated surfaces). The activation took place using the cross-linked antibody OKT-3 (Orthoclone-Diagnostics) at 20 ng/ml.

huRPMI-P:
RPMI 1640 (2 mM glutamine) without phosphate (Life Tec., 11877-032)
10% human, heat inactivated AB-Serum (HLA-A2.1 seropositive)
25 mMHEPES
1× penicillin/streptomycin (Life Tec.)

The plates were incubated in an incubator at 37° C. and 5% $CO_2$.

Co-Cultivation

For co-cultivation, the activated PBLs from the respective recesses of a 24-well-plate are pooled and counted. Adherent monocytes were discarded. The cells were centrifuged off (1500 rpm, 5 min, RT) and taken up in a concentration of $2.5*10^6$ cells/ml in fresh huRPMI-P, and placed back into the incubator. The medium was adjusted beforehand to 400 U/ml IL-2 (Chiron) and 5 µg/ml polybrene (Sigma).

6 h after the exchange of the medium, each transfection preparation was trypsinized one after the other: for this, each T25 was washed with 3 ml HBSS (Life Technologies), incubated with 1 ml of trypsin-EDTA (Life Technologies) for a maximum of 5 minutes; the dissolved cells were quantitatively taken up, and dripped with stirring into 4 ml huRPMI-P(RT) as provided. The 293T cells were irradiated with 2500 Rad. These were centrifuged off (1500 rpm, 5 min, RT) and resuspended in 4 ml fresh, adjusted huRPMI-P, supplemented with 400 U/ml IL-2 and 5 µg/ml polybrene. To the preparation, 1 ml of the adjusted PBLs were added, and the preparation ($0.5*10^6$ PBLs/ml) was incubated for three days in the incubator (37° C., 5% $CO_2$).

At day 3 after co-cultivation, the suspended PBLs were taken off and resuspended at $1*10^6$ cells/ml in fresh medium huRPMI-P that was supplemented with 40 U/ml IL-2 (Chiron) and 2.5 µl CD3/CD28-beads. 3 days later, another split into fresh medium took place. During these 7 days, a maximal expansion took place up to the transfer into T75-flasks. These cells could be directly used in an immunological staining (FACS-analysis) or in a classical $^{51}$chromium-release test.

Examples of the FACS-Analysis

Following retroviral transduction, the above-described constructs were analyzed in "fluorescence activated cell sorting" (FACS). For this, $0.25*10^6$ cells were satiable dyed with fluorophor-labeled antibodies: the heterologously expressed TCR was detected with an anti-gp100.280-288-specific tetramer, a multimer of peptide loaded HLA-A2.1-molecules; and the distribution of the T-cells to $CD4^+/CD8^+$ by the marker anti-CD4-FITC (Coulter-Beckman). A sample transduced with the empty pStitch-derivative served as a negative control (mock). The expression could be reproduced in several donors of HLA-A2-positive T-cells. The tetramers were synthesized in the laboratory of Prof. P. Romero (University Lausanne, Switzerland) (26).

Cytolytic Activity of the Transduced T-Cells

The transduced T-cells were assayed in a classical $^{51}$chromium-release test for their cytotoxic specificity. In this system, the target cells are radioactively labeled by the incorporation of $^{51}$chromium. When the retrovirally modified effector cells recognized the target cell in a peptide-specific manner, the latter is driven into apoptosis by the effector functions of the T-cell, and killed through lysis. The extent of the released chromium-nuclide is an indication for the efficiency of the cellular recognition and lysis. The efficiency was tested over a broad range of the ratios of effector-cells to target cells (E:T) as employed, and was corrected to Tetgp110⁺CD8⁺:T. The wild type gp100.280-288 specific double chain-TCR served as reference, from which the chimeric single chain-TCR was produced. The target cell as used was: T2: human TAP-deficient cell line that was to be exogeneously loaded with arbitrary peptide. The specifically mutated peptide was MDM2-81-88, an irrelevant control-peptide was derived from the HIV-polymerase (AS 510-518).

LITERATURE AS CITED

1. Schumacher, T. N. (2002) Nat. Rev. Immunol. 2, 512-519.
2. Eshhar, Z., Waks, T., Gross, G. & Schindler, D. G. (1993) Proc. Natl. Acad. Sci. U.S. A 90, 720-724.
3. Chung, S., Wucherpfennig, K. W., Friedman, S. M., Hafler, D. A. & Strominger, J. L. (1994) Proc. Natl. Acad. Sci. U.S. A 91, 12654-12658.
4. Willemsen, R. A., Weijtens, M. E., Ronteltap, C., Eshhar, Z., Gratama, J. W., Chames, P. & Bolhuis, R. L. (2000) Gene Ther. 7, 1369-1377.
5. Willcox, B. E., Gao, G. F., Wyer, J. R., O'Callaghan, C. A., Boulter, J. M., Jones, E. Y., van der Merwe, P. A., Bell, J. I. & Jakobsen, B. K. (1999) Protein Sci. 8, 2418-2423.
6. Mosquera, L. A., Card, K. F., Price-Schiavi, S. A., Belmont, H. J., Liu, B., Builes, J., Zhu, X., Chavaillaz, P. A., Lee, H. I., Jiao, J. A. et al. (2005) J. Immunol. 174, 4381-4388.
7. Weijtens, M. E., Willemsen, R. A., van Krimpen, B. A. & Bolhuis, R. L. (1998) Int. J Cancer 77, 181-187.
8. Hombach, A., Heuser, C., Gerken, M., Fischer, B., Lewalter, K., Diehl, V., Pohl, C. & Abken, H. (2000) Gene Ther. 7, 1067-1075.
9. Zhang, T., He, X., Tsang, T. C. & Harris, D. T. (2004) Cancer Gene Ther. 11, 487-496.
10. Li, Y., Moysey, R., Molloy, P. E., Vuidepot, A. L., Mahon, T., Baston, E., Dunn, S., Liddy, N., Jacob, J., Jakobsen, B. K. et al. (2005) Nat. Biotechnol. 23, 349-354.
11. Tartaglia, J., Bonnet, M. C., Berinstein, N., Barber, B., Klein, M. & Moingeon, P. (2001) Vaccine 19, 2571-2575.
12. Kalergis, A. M., Boucheron, N., Doucey, M. A., Palmieri, E., Goyarts, E. C., Vegh, Z., Luescher, I. F. & Nathenson, S. G. (2001) Nat. Immunol. 2, 229-234.
13. Voss, R. H., Kuball, J. & Theobald, M. (2005) Methods Mol. Med. 109, 229-256.
14. Voss, R. H., Kuball, J., Engel, R., Guillaume, P., Romero, P., Huber, C. & Theobald, M. (2006) Immunol. Res. 34, 67-87.
15. Rubinstein, M. P., Kadima, A. N., Salem, M. L., Nguyen, C. L., Gillanders, W. E., Nishimura, M. 1. & Cole, D. J. (2003) J. Immunol. 170, 1209-1217.
16. Call, M. E., Pyrdol, J., Wiedmann, M. & Wucherpfennig, K. W. (2002) Cell 111, 967-979.
17. Bullock, T. N., Mullins, D. W., Colella, T. A. & Engelhard, V. H. (2001) J. Immunol. 167, 5824-5831.
18. Roberts, M. R., Qin, L., Zhang, D., Smith, D. H., Tran, A. C., Dull, T. J., Groopman, J. E., Capon, D. J., Byrn, R. A. & Finer, M. H. (1994) Blood 84, 2878-2889.
19. Fitzer-Attas C. J., Schindler, D. G., Waks, T. & Eshhar, Z. (1998) J. Immunol. 160, 145-154.
20. Whitlow, M., Bell, B. A., Feng, S. L., Filpula, D., Hardman, K. D., Hubert, S. L., Rollence, M. L., Wood, J. F., Schott, M. E., Milenic, D. E. et al. (1993) Protein Eng 6, 989-995.
21. Robinson, C. R. & Sauer, R. T. (1998) Proc. Natl. Acad. Sci. U.S. A 95, 5929-5934.
22. Rees, S., Coote, J., Stables, J., Goodson, S., Harris, S. & Lee, M. G. (1996) Biotechniques 20, 102-110.
23. Cavazzana-Calvo, M., Hacein-Bey, S., de Saint, B. G., Gross, F., Yvon, E., Nusbaum, P., Selz, F., Hue, C., Certain, S., Casanova, J. L. et al. (2000) Science 288, 669-672.
24. Yant, S. R., Meuse, L., Chiu, W., Ivies, Z., lzsvak, Z. & Kay, M. A. (2000) Nat. Ge-net. 25, 35-41.
25. Bolliger, L. & Johansson, B. (1999) J. Immunol. 163, 3867-3876.
26. Robert, B., Guillaume, P., Luescher, I., Romero, P. & Mach, J. P. (2000) Eur. J. Immunol. 30, 3165-3170.

The invention claimed is:

1. A method for producing an scARC expressing cell, the method comprising:
   a) providing a suitable cell,
   b) providing a first genetic construct comprising the domains $V_{1/2}$-Li-$V_{2/1}$-$C_{4/3}$, $V_1$-Li-$V_2$-$C_4$ or $V_2$-Li-$V_1$-$C_3$ and providing a second genetic construct comprising the corresponding hetero-/(homo-)dimeric domain $C_{3/4}$, $C_{3/4}$, containing xenogenic amino acid exchanges in the domains $C_{4/3}$ and $C_3/_4$, and wherein the linker Li represents an arbitrary peptide sequence,
   c) introducing directly or indirectly the first and the second genetic constructs via viral or non-viral gene transfer into the cell, and
   d) co-expressing the first and the second genetic constructs in the cell,
   wherein the scARC is a single chain T-cell receptor (scTCR) and wherein only the ecto-subdomain of the constant domains contain the xenogenic amino acid exchanges.

2. The method according to claim 1, further comprising the presentation of the stabilized heterodimeric scTCR by the cell.

3. The method according to claim 1, wherein said scTCR is of mammalian origin in the variable domains or is of original mammalian origin.

4. The method according to claim 1, wherein said scTCR has a human sequence in the variable domains or is of original human origin.

5. The method according to claim 1, wherein said scTCR is fully or partially murinized in the ecto-subdomain of the constant domains.

6. The method according to claim 1, wherein said cell is a human T-cell.

7. The method according to claim 1, wherein said scTCR is co-expressed in the orientation SP-Vα-linker-Vβ-Cβ together with the constant domain SP-Cα, or the scARC is co-expressed in the orientation SP-Vβ-linker-Vα-Cα together with the constant domain SP-Cβ.

8. The method according to claim 1, wherein said linker (Li) is selected from Li(Gly$_4$Ser)$_3$, Li218 and LiSL7.

9. The method according to claim 1, wherein said scTCR is provided with additional functional domains or said scTCR is provided with alternative domains.

10. The method according to claim 9, wherein said scTCR is an alpha/beta scTCR or, gamma/delta scTCR, the scTCR provided with additional functional domains or the scTCR provided with alternative domains.

11. The method according to claim 10, wherein the alpha- and beta-chains of a gp 100(280-288)-specific TCR are used as alpha-chain and beta-chain.

12. The method according to claim 1, wherein a retroviral vector is used for viral gene transfer.

13. The method according to claim 1, further comprising the purification of the scTCR from the cell.

14. The method according to claim 13, further comprising the reconstitution of the translated scTCR- fragments in a T-cell.

15. The method, according to claim 1, wherein the genetic construct comprising the hetero-/(homo-)dimeric domain $C_{374}$, $C_3$ or $C_4$, comprises specific targeted xenogenic amino acid exchanges in the ecto-subdomain of the constant domains.

16. A method for producing an scARC expressing cell, the method comprising:
   a) providing a suitable cell,
   b) providing a first genetic construct comprising the domains $V_{1/2}$-Li-$V_{2/1}$-$C_{4/3}$, $V_1$-Li-$V_2$-$C_4$ or $V_2$-Li-$V_1$-$C_3$ and providing a second genetic construct comprising the corresponding hetero-/(homo-)dimeric domain $C_{3/4}$, $C_3$ or $C_4$, containing xenogenic amino acid exchanges in the domains $C_{4/3}$ and $C_{3/4}$, and wherein the linker Li represents an arbitrary peptide sequence,
   c) introducing directly or indirectly the first and the second genetic constructs via viral or non-viral gene transfer into the cell, and
   d) co-expressing the first and the second genetic constructs in the cell, wherein the scARC is an scTCR and wherein said scTCR contains xenogenic point mutations in the constant domains.

17. The method according to claim 16, further comprising the presentation of the stabilized heterodimeric scTCR by the cell.

18. The method according to claim 16, wherein said scTCR is of mammalian origin in the variable domains or is of original mammalian origin.

19. The method according to claim 16, wherein said scTCR has a human sequence in the variable domains or is of original human origin.

20. The method of according to claim 16, wherein said cell is a human T-cell.

21. The method according to claim 16, wherein said scTCR is co-expressed in the orientation SP-Vα-linker-Vβ-Cβ together with the constant domain SP-Cα, or the scTCR is co-expressed in the orientation SP-Vβ-linker-Vα-Cα together with the constant domain SP-Cβ.

22. The method according to claim 16, wherein said linker (Li) is selected from Li(Gly$_4$Ser)$_3$, Li218 and LiSL7.

23. The method according to claim 16, wherein said scTCR is provided with additional functional domains or said scTCR is provided with alternative domains.

24. The method according to claim 23, wherein said scTCR is an alpha/beta scTCR or, gamma/delta scTCR, the scTCR provided with additional functional domains, or the scTCR provided with alternative domains.

25. The method according to claim 24, wherein the alpha- and beta-chains of a gp 100(280-288)-specific TCR are used as alpha-chain and beta-chain.

26. The method according to claim 16, wherein a retroviral vector is used for viral gene transfer.

27. The method according to claim 16, further comprising the purification of the scTCR from the cell.

28. The method according to claim 27, further comprising the reconstitution of the translated scTCR-fragments in a T-cell.

29. The method according to claim 16, wherein said scTCR is fully or partially murinized in the ecto-domain of the constant domains.

30. The method according to claim 16, wherein the xenogenic point mutations are specific targeted xenogenic point mutations in the ecto-subdomain of the constant domains.

* * * * *